US009925140B2

(12) United States Patent
Huang

(10) Patent No.: US 9,925,140 B2

(45) **Date of Patent: *Mar. 27, 2018**

(54) CELL TISSUE GEL CONTAINING COLLAGEN AND HYALURONAN

(71) Applicant: National Cheng Kung University, Tainan (TW)

(72) Inventor: Lynn L. H. Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/445,944

(22) Filed: Jul. 29, 2014

(65) Prior Publication Data

US 2014/0341866 A1 Nov. 20, 2014

Related U.S. Application Data

(63) Continuation-in-part of application No. 12/974,535, filed on Dec. 21, 2010, now Pat. No. 8,790,683.

(60) Provisional application No. 61/289,132, filed on Dec. 22, 2009.

(51) Int. Cl.

| | |
|---|---|
| ***A61F 2/00*** | (2006.01) |
| ***A01N 63/00*** | (2006.01) |
| ***A01N 65/00*** | (2009.01) |
| ***C12N 11/00*** | (2006.01) |
| ***C12N 5/02*** | (2006.01) |
| ***A61L 27/26*** | (2006.01) |
| ***A61K 9/06*** | (2006.01) |
| ***A61K 35/50*** | (2015.01) |
| ***A61L 27/38*** | (2006.01) |
| ***A61L 27/52*** | (2006.01) |
| ***A61L 27/54*** | (2006.01) |
| ***A61K 35/28*** | (2015.01) |
| ***C12N 5/00*** | (2006.01) |
| ***C12N 5/073*** | (2010.01) |
| ***C12N 5/0775*** | (2010.01) |
| ***C08L 5/08*** | (2006.01) |
| ***C08L 89/06*** | (2006.01) |

(52) U.S. Cl.

CPC ................ *A61K 9/06* (2013.01); *A61K 35/28* (2013.01); *A61K 35/50* (2013.01); *A61L 27/26* (2013.01); *A61L 27/3834* (2013.01); *A61L 27/52* (2013.01); *A61L 27/54* (2013.01); *C08L 5/08* (2013.01); *C08L 89/06* (2013.01); *C12N 5/0068* (2013.01); *C12N 5/0605* (2013.01); *C12N 5/0668* (2013.01); *A61L 2300/414* (2013.01); *C12N 2533/54* (2013.01); *C12N 2533/76* (2013.01); *C12N 2533/80* (2013.01)

(58) Field of Classification Search

None

See application file for complete search history.

(56) References Cited

U.S. PATENT DOCUMENTS

| | | | | |
|---|---|---|---|---|
| 6,773,723 | B1 | 8/2004 | Spiro et al. | |
| 2005/0027069 | A1* | 2/2005 | Rhee et al. | 525/54.1 |
| 2005/0113937 | A1 | 5/2005 | Binette et al. | |
| 2006/0018946 | A1 | 1/2006 | Prescott | |
| 2006/0068013 | A1* | 3/2006 | DiTizio et al. | 424/484 |
| 2006/0233850 | A1 | 10/2006 | Michal | |
| 2007/0116680 | A1 | 5/2007 | Stegemann et al. | |
| 2009/0076624 | A1 | 3/2009 | Rahaman et al. | |
| 2009/0093755 | A1 | 4/2009 | Schroeder et al. | |
| 2009/0098110 | A1 | 4/2009 | Adams et al. | |
| 2009/0305415 | A1 | 12/2009 | Huang | |
| 2009/0305416 | A1 | 12/2009 | Huang | |

OTHER PUBLICATIONS

Kuenzler, JF. 2002. "Hydrogels." in: Encyclopedia of Polymer Science and Technology (Mark, HF, ed. pp. 691-722.*

Bellows et al "Determination of Numbers Of Osetoprógenitors Present in isolated Fetal Rat Calvaria Cells in Vitro" Developmental Biology vol. 33, pp. 8-13. 1989.

Angele et al "Engineering of Osteochondral Tissue with Bone Marrow Mesenchymal Progenitor Cells in a Derivatized Hyaluronan-Gelatin Composite Sponge" Tissue Engineering vol. 5, pp. 545-553. 1999.

Lee et al "Hydrogels for Tissue Engineering" Chemical Reviews vol. 101, pp. 1869-1879. 2001.

Crevensten et al "Intervertebral Disc Cell Therapy for Regeneration: Mesenchymal Stem Cell Implantation in Rat Intervertebral Discs" Annals of Biomedical Engineering vol. 32, pp. 430-434. 2004.

Liu et al "Osteochondral Defect Repair with Autologous Bone Marrow-Derived Mesenchymal Stem Cells in an Injectable, in Situ, Cross-Linked Synthetic Extracellular Matrix" Tissue Engineering vol. 12, pp. 3405-3420. 2006.

Kogan et al "Hyaluronic Acid: A Natural Biopolymer with a Broad Range of Biomedical and Industrial Applications" Biotechnology Letters vol. 29, pp. 17-25. 2007.

Noth et al "Chondrogenic Differentiation of Human Mesenchymal Stem Cells in Collagen Type I Hydrogels" Journal of Biomedical Materials Research vol. 83, pp. 626-635. 2007.

Chen et al "Hyaluronan Preserves the Proliferation and Differentiation Potentials of Long-Term Cultured Murine Adipose-Derived Stromal Cells" Biomedical and Biophysical Research Communications vol. 360, pp. 1-6. 2007.

Liu et al "Hyaluronan Substratum Holds Mesenchymal Stem Cells in Slow-Cycling Mode by Prolonging G1 Phase" Cell and Tissue Research vol. 334, pp. 435-443. 2008.

(Continued)

*Primary Examiner* — Maria Leavitt

(74) *Attorney, Agent, or Firm* — Cesari and McKenna, LLP

(57) ABSTRACT

Described herein is a cell tissue gel containing collagen and hyaluronan at a weight ratio of 0.01-100:1.

10 Claims, 11 Drawing Sheets

(56) References Cited

OTHER PUBLICATIONS

Pardue et al "Role of Hyaluronan in Angiogenesis and its Utility to Angiogenic Tissue Engineering" Organogenesis vol. 4, pp. 203-214. 2008.
Liu et al "Hyaluronan Substratum Induces Multidrug Resistance in Human Mesenchymal Stem Cells via CD44 Signaling" Cell and Tissue Research vol. 336, pp. 465-475. 2009.
Yan et al "Recovery From Hind Limb Ischemia is Less Effective in Type 2 than in Type 1 Diabetic Mice: Roles of Endothelial Nitric Oxide Synthase and Endothelial Progenitor Cells" Journal of Vascular Surgery vol. 50, pp. 1412-1422. 2009.
Hahn, et al., "Collagen composite hydrogels for vocal fold lamina propria restoration", Biomaterials 27 (2006) 1104-1109.
Liao, et al., "Tissue-Engineered Cartilage Constructs Using Composite Hyaluronic Acid/Collagen I Hydrogels and Designed Poly(Propylene Fumarate) Scaffolds" Tissue Engineering, vol. 13, No. 3, 2007, 537-550.
Lin, et al., "Synthesis and characterization of collagen/hyaluronan/chitosan composite sponges for potential biomedical applications", Acta Biomaterialia 5 (2009) 2591-2600.
Prestwich, et al., "Biomaterials from Chemically-Modified Hyaluronan", Feb. 26, 2001, Glycoforum.

* cited by examiner

A

B

A

B

A

B

A

B

A

B

A

B

A

B

CELL TISSUE GEL CONTAINING COLLAGEN AND HYALURONAN

CROSS-REFERENCE TO RELATED APPLICATIONS

This application is a continuation-in-part of U.S. patent application Ser. No. 12/974,535, filed on Dec. 21, 2010, now issued as U.S. Pat. No. 8,790,683, which claims priority to U.S. Provisional Patent Application Ser. No. 61/289,132, filed on Dec. 22, 2009. The contents of all prior applications are hereby incorporated by reference in their entirety.

BACKGROUND

Stem cell therapy is a promising approach in treating degenerative diseases. However, it remains challenging to retain stem cells at an implantation site and maintain their viability in a recipient so as to affect tissue repair. There is a need for a vehicle (e.g., a cell tissue gel) that facilitates site-specific stem cell implantation with high cell viability.

Wound healing is a natural restorative response to tissue injury. Healing is the interaction of a complex cascade of cellular events that generates resurfacing, reconstitution, and restoration of the tensile strength of injured skin. In diabetic patients, wounds can take longer to heal than non-diabetic patients.

SUMMARY

Described herein is a cell tissue gel containing collagen and hyaluronan at a weight ratio of 0.01-100 (collagen):1 (hyaluronan), e.g., 0.05-100:1, 1-50:1, 100:1, 75:1, 50:1, 30:1, 25:1, 15:1, 10:1, 5:1, 1:1, 0.5:1, 0.2:1, or 0.1:1. The concentration of the hyaluronan can be 0.001 to 100 mg/ml (e.g., 0.01 to 1 mg/ml, 0.5 to 100 mg/ml, 0.5 mg/ml, 1 mg/ml, 1.5 mg/ml, 3 mg/ml, 5 mg/ml, 10 mg/ml, 15 mg/ml, 20 mg/ml 25 mg/ml, 30 mg/ml, 50 mg/ml, 75 mg/ml, or 100 mg/ml). The concentration of collagen can be 0.001 to 100 mg/ml (e.g., 1-100 mg/ml, 10-100 mg/ml, 100 mg/ml, 75 mg/ml, 50 mg/ml, 30 mg/ml, 25 mg/ml, 15 mg/ml, 10 mg/ml, or 5 mg/ml). For example, the collagen concentration can be 0.1 to 100 mg/ml and the hyaluronan concentration can be 0.01 to 35 mg/ml. In one embodiment, the collagen concentration is 3 to 40 mg/ml (e.g., 6 mg/ml or 9 mg/ml) and the hyaluronan concentration is 0.2 to 20 mg/ml. In another embodiment, the concentration of the hyaluronan is 0.5 to 100 mg/ml and the concentration of the collagen is 5 to 50 mg/ml.

The cell tissue gel of this invention can further contain a nutrient for cell growth (e.g., a cell culture medium or a vitamin), a bioactive agent, one or more matrix factors, and/or stem cells. The bioactive agent can be a growth factor, e.g., epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte macrophase colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor. Exemplary matrix factors include, but are not limited to, gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, and glycogen. When the cell tissue gel contains gelatin, its concentration can range from 0.01-100 mg/ml (e.g., 1 mg/ml). The collagen and hyaluronan concentrations in this gelatin-containing gel can be 6-40 mg/ml and 0.2-20 mg/ml, respectively.

Also described is a method of delivering cells (e.g., stem cells) into a subject, including (i) providing a cell implant containing the cell tissue gel described above, in which cells grow, and (ii) placing the cell implant in a site of the subject. Also within the scope of this invention is use of the cell tissue gel in manufacturing a cell implant used in cell delivery.

The cell tissue gel described herein can be applied to a wound in a subject to treat or promote healing of the wound.

The details of one or more embodiments of the invention are set forth in the description below. Other features or advantages of the present invention will be apparent from the following detailed description of an example and also from the appended claims.

DETAILED DESCRIPTION

Figure 1:
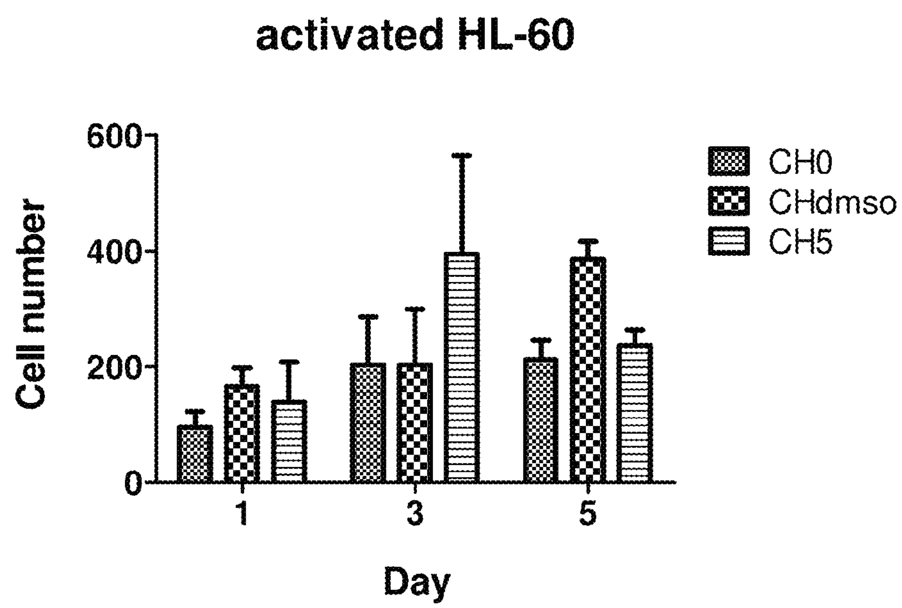
FIG. 1 is a set of two bar graphs showing the effects of various tissue gels containing collagen and hyaluronan on inflammatory cells. CH0—50 mg/mL collagen with no hyaluronan; CH5—50 mg/mL collagen+5 mg/mL hyaluronan; CHpma—50 mg/mL collagen+phorbol myristate acetate (PMA). A. activated HL-60 cells. B. U937 cells.
Figure 1:
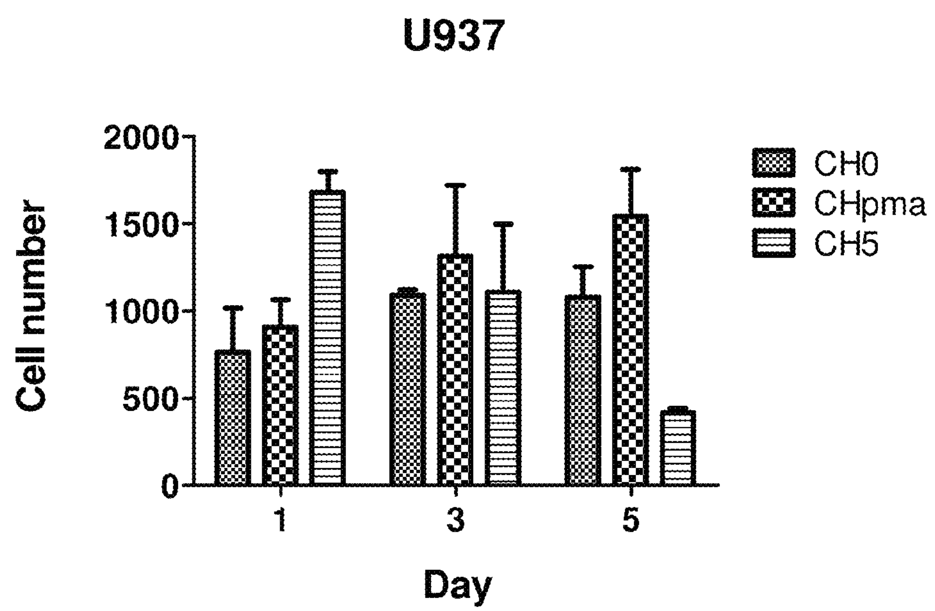

Described herein is a tissue gel containing collagen and hyaluronan at a weight ratio of 0.01-100 to 1 (e.g., 0.05-100:1, 1-50:1, 100:1, 75:1, 50:1, 30:1, 25:1, 15:1, 10:1, 5:1, 1:1, 0.5:1, 0.2:1, or 0.1:1), and optionally one or more other components such as a matrix factor, a bioactive agent, and a nutrient for cell growth.

Collagen

Any of the naturally-occurring collagens or their functional variants can be used for preparing the tissue gel of this invention. At the present time, at least 28 genetically distinct species of collagens have been discovered. Collagen can be easily isolated and purified from collagen-rich tissues such as skin, tendon, ligament, and bone of humans and animals. Methods for isolating and purifying collagen are well known in the art. (See, e.g., U.S. Pat. No. 5,512,291; US Patent Publication 20040138695; Methods in Enzymology, vol. 82, pp. 33-64, 1982; The Preparation of Highly Purified Insoluble Collagen, Oneson, I., et al., Am. Leather Chemists Assoc., Vol. LXV, pp. 440-450, 1970; U.S. Pat. No. 6,090, 996). Collagen can also be prepared by recombinant technology, such as those described by Advanced Tissue Sciences (La Jolla, Calif.) or purchased from various venders (e.g., Fibrogen; South San Francisco, Calif.). One example follows. Bovine deep flexor tendons, with fat and fascia removed, are washed with water, frozen, and sliced into 0.5 mm slices with a slicer. A suitable amount of the sliced tendons is first extracted with 50 ml of water at room temperature for 24 hours. The water-soluble fraction is discarded and the sliced tendons are then extracted with an acidic solution (e.g., 0.2 N HCl) at a suitable temperature (e.g., room temperature) for a suitable period of time (e.g., 12-24 hours). The HCl solution is discarded; the tendons rinsed with water to remove the residual acid. The rinsed tendons are then extracted with a basic solution (e.g., 0.75 M NaOH) at a suitable temperature (e.g., room temperature) for a suitable period of time (e.g., 12-24 hours). After discarding the basic solution, the sliced tendons are neutralized with an acidic solution (e.g., 0.1 N HCl) to a pH of 4-7 (e.g. 5) followed by repetitive washes with water to remove the residual base in the tendons. The tendons are then defatted with an alcohol (e.g., isopropanol) for a sufficient period (e.g., 16 hours) at room temperature. The extractant is decanted and the tendons are further extracted with an alcohol (e.g., isopropanol) for a suitable period (e.g., 12-24 hours) at room temperature to form a collagen-containing solution, which can be dried under a clean hood. The collagen powder thus formed can be dispersed in an acidic solution (e.g., 0.5 M or 0.25 M acetic acid) in the presence of a proteolytic enzyme (e.g., trypsin or pepsin) and incubated at 4° C. for a suitable period. The mixture is then filtered through a 100 mesh stainless steel mesh filter and the solubilized collagen can be precipitated with a 5% NaCl solution. The precipitated collagen can be redissolved in the acidic solution described above and the solution thus formed can be filtered through a 100 mesh stainless steel mesh filter to eliminate non-solubilized particles. The collagen solution is then dialyzed with distilled water to remove the acid.

Hyaluronan

The term "hyaluronan" refers to a naturally-occurring anionic, non-sulfated glycosaminoglycan including repeated disaccharide units of N-acetylglucosamine and D-glucuronic acid, and its derivative. Naturally-occurring hyaluronan (also known as hyaluronic acid or hyaluronate) can be isolated from its natural sources, e.g., capsules of Streptococci, rooster comb, cartilage, synovial joints fluid, umbilical cord, skin tissue and vitreous of eyes, via conventional methods. See, e.g., Guillermo Lago et al. Carbohydrate Polymers 62(4): 321-326, 2005; and Ichika Amagai et al. Fisheries Science 75(3): 805-810, 2009. Alternatively, it can be purchased from a commercial vendor, e.g., Genzyme Corporation, Lifecore Biomedical, LLC and Hyaluron Contract Manufacturing. Derivatives of naturally-occurring hyaluronan include, but are not limited to, hyaluronan esters, adipic dihydrazide-modified hyaluronan, hyaluronan amide products, crosslinked hyaluronic acid, hemiesters of succinic acid or heavy metal salts thereof hyaluronic acid, partial or total esters of hyaluronic acid, sulphated hyaluronic acid, N-sulphated hyaluronic acid, and amines or diamines modified hyaluronic acid. They can be obtained by chemically modifying one or more of its functional groups (e.g., carboxylic acid group, hydroxyl group, reducing end group, N-acetyl group). A carboxyl group can be modified via esterification or reactions mediated by carbodiimid and bishydrazide. Modifications of hydroxyl groups include, but are not limited to, sulfation, esterification, isourea coupling, cyanogen bromide activation, and periodate oxidation. A reducing end group can be modified by reductive amination. It also can be linked to a phospholipid, a dye (e.g., a fluorophore or chromophore), or an agent suitable for preparation of affinity matrices. Derivatives of naturally-occurring hyaluronan can also be obtained by crosslinking, using a crosslinking agent (e.g., bisepoxide, divinylsulfone, biscarbodiimide, small homobifunctional linker, formaldehyde, cyclohexyl isocyanide, and lysine ethyl ester, metal cation, hydrazide, or a mixture thereof) or via internal esterification, photocross-linking, or surface plasma treatment.

Nutrient for Cell Growth

The term "nutrient" refers to a source of nourishment essential for cell growth. It can be an amino acid, vitamin, mineral, carbon source (e.g., glucose), fatty acid, or a mixture thereof. In one example, the nutrient used in the tissue gel of this invention is a cell growth medium, e.g., Minimum Essential Medium, Basal Medium Eagle, Dulbecco's Modified Eagle's medium, Ham's Nutrient Mixtures F-10 or F-12, Medium 199, RPMI medium, Ames' Media, BGJb Medium (Fitton-Jackson Modification), Click's Medium, CMRL-1066 Medium, Fischer's Medium, Glascow Minimum Essential Medium, Iscove's Modified Dulbecco's Medium, L-15 Medium, McCoy's 5A Modified Medium, NCTC Medium, Swim's S-77 Medium, Waymouth Medium, or William's Medium E.

Bioactive Agent

Any agent (e.g., peptide, polypeptide, oligosaccharide, polysaccharide, or small molecule) that improves cell viability, promotes cell proliferation, or induces cell differentiation can be used in making the tissue gel of this invention. In one example, the bioactive agent is a growth factor, such as epidermal growth factor, fibroblast growth factor, vascular endothelial growth factor, connective tissue growth factor, platelet-derived growth factor, insulin-like growth factor, nerve growth factor, hepatocyte growth factor, colony-stimulating factors, stem cell factor, serotonin, and von Willebrand factor, transforming growth factor, keratinocyte growth factor, granulocyte colony-stimulating factor, granulocyte/macrophage colony stimulating factor, glial derived neurotrophic factor, ciliary neurotrophic factor, endothelial-monocyte activating polypeptide, epithelial neutrophil activating peptide, erythropoietin, bone morphogenetic proteins, brain-derived neurotrophic factor. In another example, the bioactive agent is a cytokine or chemokine, including, but are not limited to, IL-2, breast-expressed chemokine (e.g., BRAK), kidney-expressed chemokine (e.g., CXCL14). The bioactive agent can also be a cell differentiation factor, such as dexamethasone, sodium pyruvate, ascorbic acid-2-phosphate, retinoic acid, proline, insuline, transferrin, selenous acid, linoleic acid, and bovine serum albumin, and TGF-β3. In a preferred example, the differentiation factor is a compound that promotes chondrogenesis of mesenchymal stem cells (see those disclosed in U.S. Pat. No. 5,908,784), osteogenesis (e.g., dexamethasone, ascorbic acid, β-glycerol phosphate), adipogenesis (e.g., insulin, isobutyl-methyl xanthine, dexamethasone, indomethacin), cardiomyogenic differentiation (e.g., activin A, BMP-4), endothelial cell differentiation (e.g., EBM-2, dexamethasone, and VEGF), smooth muscle cell differentiation (e.g., PDGF-BB), neural induction (e.g., bFGF, EGF, and B27 supplement, DMSO, butylated hydroxyanisole, forskolin, valproic acid, KCl, K252a, and N2 supplement) and endodermal lineage differentiation (e.g., dexamethasone, HGF, and FGF-4). The bioactive agent can also be a Chinese herbal medicine or an active ingredient thereof.

Matrix Factor

A matrix factor is a compound that helps retain cells at an implantation site. It can be an extracellular factor found in the extracellular matrix. Examples are, but are not limited to, gelatin, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, glycogen and derivatives thereof. In addition, the matrix factor can be fibrin, fibrinogen, thrombin, and polyglutamic acid, a synthetic polymer (e.g., acrylate, polylactic acid, polyglycolic acid, or poly(lactic-co-glycolic acid), or a cross-linking agent (e.g., genipin, glutaraldehyde, formaldehyde, or epoxide). It is preferred that the matrix factor used in the tissue gel described herein has a high molecular weight so as to increase the viscosity of the gel.

Excipient

The cell tissue gel described herein can include one or more pharmaceutically acceptable excipients to provide lubrication and moisture insulation. The presence of the excipient can also serve as a cream to bind and smooth the epithelial layer for healing of shallow wounds.

Lecithin, petroleum jelly, glycerol, glycerine, and glycerin are exemplary excipients that can be included in the cell tissue gel. Other excipients are also known and available in the art.

Preparation of Tissue Gels with Cell Embedded

The tissue gel described herein can be prepared by mixing all of its components mentioned above at a desired weight ratio and keeping the mixture under suitable conditions to allow gel formation. To prepare a cell-embedded gel, desired cells can be mixed with the gel components prior to gel formation. The cells can be stem cells obtained from a mammal (e.g., bovine, porcine, murine, equine, canine, feline, ovine, simian, and human). Examples are, but are not limited to, placenta-derived stem cells, bone marrow-derived stem cells, stromal cells (e.g., adipose-derived stromal cells), mesenchymal stem cells, tissue progenitor cells, blast cells, or fibroblasts.

The tissue gel thus prepared, with cells embedded, can be implanted to a desired site for tissue repair and other therapeutic purposes.

Wound Healing

The cell tissue gel described herein, with or without cells embedded, can be used to treat or promote healing of a wound (e.g., skin wound). The cell tissue gel can be applied to the wound such that it partially, substantially, or completely covers the wounded area. In particular, the tissue gel can be used to treat a wound in a diabetic patient. The wound can be shallow wound, a partial wound, or a full-thickness wound.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1: Stem Cell Viability in Tissue Gels Containing Collagen and Hyaluronan Chorionic villi were obtained from full-term human placentas, mechanically minced, and then digested with colagenase to obtain a material containing placenta-derived mesenchymal stem cells. The material was passed through sieves having mesh sizes of 300-, 100-, and 37-μm sequentially and then subjected to percoll density gradient centrifugation to collect stem cells. The cells were suspended in 2× low glucose Dulbecco's Modified Eagle's Medium (Gibco BRL, Life Technologies) supplemented with 20% fetal bovine serum and 200 U/ml gentamycin, at a concentration of $10^5$-$10^7$ cells/ml, and mixed with various amounts of hyaluronan to form a suspension. Collagen, obtained from porcine dermis, was dissolved in 0.01 N HCl to form a collagen solution having a pH of 4-7. The collagen solution was mixed with the stem cell-containing suspension at an equal volume to form a mixture having 6 mg/ml of collagen and 0.05 mg/ml, 0.2 mg/ml, or 0.5 mg/ml of hyaluronan, or 9 mg/ml of collagen and 0.2 mg/ml of hyaluronan. Mixtures containing collagen at 6 mg/ml and 9 mg/ml and the same amount of stem cells were used as controls. Any of the above-described mixtures were kept at 37° C. of incubator for 30 minutes to allow collagen solidification so as to form a tissue gel embedded with stem cells. The tissue gel was cultured at 37° C. with 5% $CO_2$ supply for up to 14 days. Cell viabilities at different time point (e.g., day 1, day 7, and day 14) were examined by trypan blue staining. The results thus obtained are shown in Table 1 below.

As shown in Table 1, the weight ratio of collagen vs. hyaluronan in the tissue gel was critical for maintaining viability of the stem cells grown in the gel over time.

TABLE 1

Stem Cell Viability in Tissue Gels Containing Collagen and Hyaluronan

| Concentrations (mg/ml) | | Percentage of Viable Cells (%) | | |
|---|---|---|---|---|
| Collagen | Hyaluronan | Day 1 | Day 7 | Day 14 |
| 6 | 0 | 87.5 | 41.8 | 40.5 |
| 6 | 0.05 | 80 | 72.3 | 63.6 |
| 6 | 0.2 | 85.1 | 73.2 | 75.3 |
| 6 | 0.5 | 70.8 | 43.4 | 57.7 |
| 9 | 0 | 96.3 ± 3.4 | N.A. | 35.7 ± 0.3 |
| 9 | 0.2 | 93.8 ± 1.0 | N.A. | 72.7 ± 10.4 |

Example 2: Stem Cell Viability in Tissue Gels Containing Collagen, Hyaluronan, and Gelatin The stem cell suspension and collagen solution described in Example 1 above were mixed at 1:1 by volume together with gelatin (2 or 10 mg/mL) to form stem cell-embedded tissue gels. Their final concentrations of collagen, hyaluronan, and gelatin are shown in Table 2 below.

The tissue gels were cultured at 37° C. with 5% $CO_2$ supply for up to 14 days. Cell viabilities at different time point (e.g., day 1, day 7, and day 14) were examined as described in Example 1 above. Table 2 below lists the percentages of viable cells grown in the tissue gels described above.

TABLE 2

Stem Cell Viability in Tissue Gels Containing Collagen, hyaluronan, and Gelatin

| Concentration (mg/ml) | | | Percentage of Viable Cells (%) | | |
|---|---|---|---|---|---|
| Collagen | hyaluronan | Gelatin | Day 1 | Day 7 | Day 14 |
| 6 | 0 | 1 | 93.1 | 43.5 | 54.7 |
| 6 | 0.05 | 1 | 87.3 | 76.8 | 49.1 |
| 6 | 0.2 | 1 | 90.2 | 71.4 | 78 |
| 6 | 0.5 | 1 | 58.5 | 55.6 | 42.4 |
| 6 | 0 | 5 | 80 | 22.1 | 41.5 |
| 6 | 0.05 | 5 | 93.2 | 40 | 46.3 |
| 6 | 0.2 | 5 | 71.9 | 42.9 | 44.4 |
| 6 | 0.5 | 5 | 44.4 | 19.1 | 33.1 |
| 9 | 0.2 | 1 | 98.0 ± 0.4 | N.A. | 47.8 ± 6.5 |

Example 3: Effects of Tissue Gels Containing Collagen and Hyaluronan on Cell Proliferation It was reported that the characteristics of activated HL-60 by 1.3% dimethyl sulfoxide (DMSO) for 7 days resemble those of activated human neutrophils that express CD11b and CD32. The activated HL-60 cells were used to study the effects of cell tissue gels on neutrophil proliferation. Activated HL-60 at $1\times10^4$ cells/well in 96-well plate were cultured in RPMI 1640 with cell tissue gels containing various concentrations of hyaluronan.

Mouse macrophage cell line RAW 264.7 was confirmed to express macrophage F4/80 and was used to study the effects of cell tissue gels on macrophage proliferation. RAW 264.7 at $3\times10^3$ cells/well in 96-well plate were cultured in DMEM-10% FBS with the cell tissue gels containing various concentrations of hyaluronan.

NIH-3T3 fibroblasts may represent cells in the stromal layer of tissues and therefore were chosen to study the effects of cell tissue gels on fibroblast proliferation. NIH-3T3 fibroblasts at $2\times10^3$ cells/well in 96-well plate was cultured in DMEM-10% FBS with the cell tissue gels containing various concentrations of hyaluronan.

After culturing the above cells in a 37° C. incubator with 5% $CO_2$ for 3 and 5 days, cells were recovered by centrifugation, bursted to expose the cell nucleus, and stained with Hoechst 33258. The fluorescent intensity was proportional to cell numbers and was measured by a SpectraMax M2e Multi-Mode Microplate Reader with excitation at 365 nm and emission at 460 nm.

The results indicated that the presence of hyaluronan in the cell tissue gels may slightly inhibit neutrophil proliferation during a prolonged period, i.e., at or after day 5. No significant effect was observed for macrophage proliferation. The constituents in cell tissue gels at various ratios of collagen to hyaluronan promoted fibroblast proliferation both at day 3 and day 5. The results imply a positive effects of the cell tissue gels on the process of wound healing.

Example 4: Effects of Tissue Gels Containing Collagen and Hyaluronan on Inflammatory Cells Activated HL-60 cells and U937 cells were used to understand the interaction of hyaluronan with human neutrophils and macrophages, respectively. Human promyelocytic HL-60 cells acquired a neutrophilic phenotype after a 7-day DMSO treatment. U937 cells mature and differentiate in response to a number of soluble stimuli, adopting the morphology and characteristics of mature macrophages.

In cell culture 24-well plates, cell tissue gels of collagen and hyaluronan at various ratios were individually added to the middle of the 1 mm silicone rings. Activated HL-60 cells and U937 cells respectively were seeded to the outside of the silicone rings. After gelation of the cell tissue gels and the adhesion of the cells, the silicone rings were removed to allow the migration and infiltration of cells across the 1 mm distance toward the cell tissue gels. At day 1, 3, and 5, the cell tissue gels were fixed with 4% paraformaldehyde followed with immunofluorescent staining of nuclear DAPI. The infiltrated cell numbers were counted using panoramic scanning microscopy.

The cell tissue gels CH0, CH5, and CHpma denote the gels containing 50 mg/mL collagen with no hyaluronan, 5 mg/mL hyaluronan, and phorbol myristate acetate (PMA) respectively. See FIG. 1. The results demonstrated that the presence of hyaluronan in cell tissue gels can stimulate the infiltration of neutrophils and macrophages at early time periods. This indicates a positive effect on facilitating the process of wound healing with the presence of hyaluronan in the cell tissue gels.

Example 5: Chemotactic Effects of Hyaluronan

Boyden chamber with 3 μm pores of membrane was used to study the chemotactic effects of hyaluronan on human neutrophils. $1\times10^5$ cells/well of activated HL-60 cells were placed in the upper chamber and 10 nM fMLP (formyl-methionyl-leucyl-phenylalanine; f-Met-Leu-Phe) or 1 mg/mL hyaluronan at various molecular weights were placed initially at the bottom chamber.

Boyden chamber with 5 μm pores of membrane was used to study the chemotactic effects of hyaluronan on macrophages. $5\times10^5$ cells/well of RAW 264.7 cells were placed in the upper chamber and 1 μg/mL LPS (lipopolysaccharide) or 1 mg/mL hyaluronan at various molecular weights were placed initially at the bottom chamber.

After culturing for 4 or 6 hours, 4% paraformaldehyde was used to fix cells on the membrane and the cells on the upper side were removed by cotton swab. The cells were stained with DAPI and quantitated under light microscopy.

Figure 2:
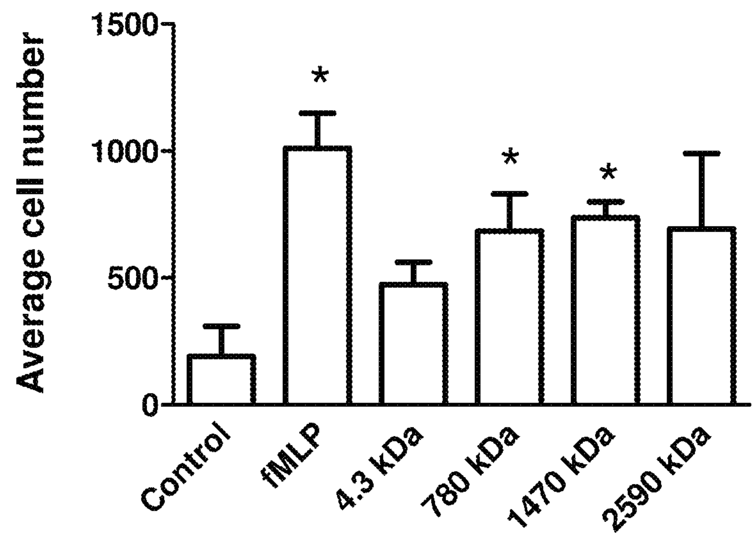
FIG. 2 is a set of two bar graphs (A and B) showing the chemotactic effects of hyaluronan of various molecular weights. A. HL-60 cells. B. RAW 264.7 cells.
Figure 2:
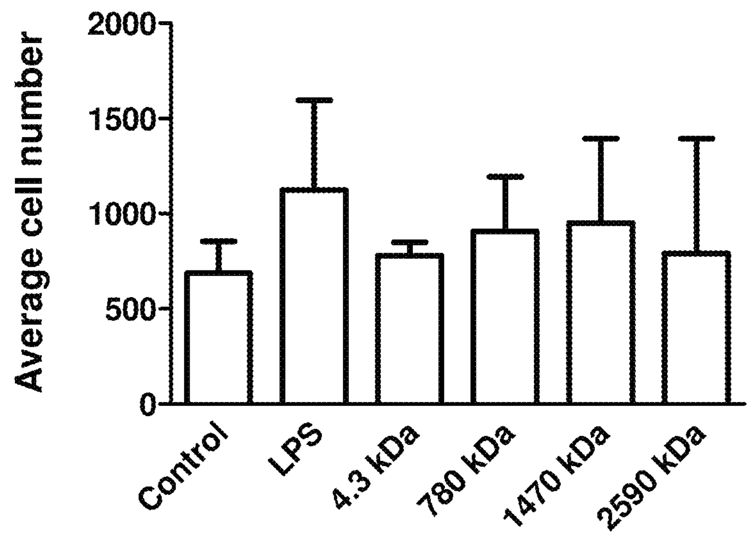
Figure 3:
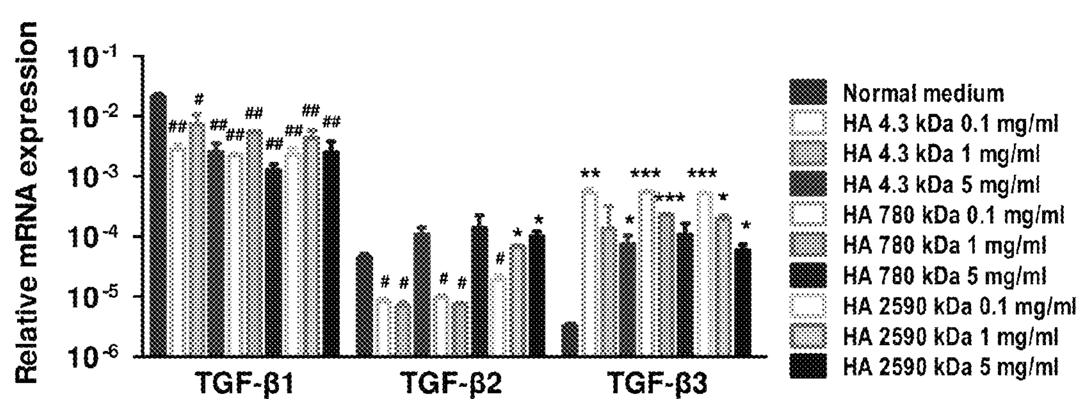
FIG. 3 is a bar graph showing the effects of hyaluronan (HA) of various molecular weights at different concentrations on TGF-β1, TGF-β2 and TGF-β3 expressions. The order shown in the legend corresponds to the order of the bars in each of the three groups, i.e., the first (leftmost) bar is normal medium and the last bar (rightmost) is HA 2590 kDa at 5 mg/ml. Comparing to the level for normal medium group, down regulation is denoted as #: $p<0.05$, ##: $p<0.005$, ###: $p<0.001$; up regulation is denoted as *: $p<0.05$, : $p<0.005$, *: $p<0.001$.

The results demonstrated a significant chemotactic effect of various molecular weights of hyaluronan on activated neutrophils. See FIG. 2. A molecular weight higher than 780 kDa seems to attract further movement of cells. Since neutrophils play more important roles in clean wounds, these data further indicate a positive effect of hyaluronan in cell tissue gels for wound applications.

Example 6: Effects of Hyaluronan on TGF-β1, TGF-β2 and TGF-β3 Expressions

Activated HL-60 cells were cultured in RPMI cultural medium containing hyaluronan at various molecular weights and concentrations. After culturing for 3 days, the mRNA expression of TGF-β1, TGF-β2 and TGF-β3 were analyzed by quantitative real-time polymerase chain reaction using appropriate gene detection primers and probes. The relative mRNA expression levels were normalized with GAPDH (glyceraldehyde 3-phosphate dehydrogenase) expression. The Roche Universal Probe Library System was used for specific detection of each gene expression and statistics t-test was analyzed for the significacy.

Our results demonstrated that the presence of hyaluronan can inhibit neutrophil expression of TGF-β1 and stimulate the expression of TGF-β3. It was reported that neutralization of TGF-β1 and TGF-β2 or the addition of TGF-β3 to cutaneous wounds not only improve architecture of the neodermis but also reduce scarring. See Shah M, Foreman D, Ferguson M., J Cell Sci 1995; 108: 985-1002. Our data suggest that cell tissue gels containing hyaluronan can result in better healing with reduced scarring.

Example 7: Effects of Cell Tissue Gels on Wound Healing

We established a mouse skin wound model with 8 mm diameter O-ring sutured on the outer of the 6 mm full-thickness circular wound to avoid over contraction of the wound. The advantage of this model is that the mode of wound closure is closer to that of human skin in which the re-epithelialization and granulation tissue formation are involved rather than rodent wounds which have excessive contraction during the healing process.

Four dorsal skin wounds were created on a FVB mouse. Various formulations of cell tissue gels were implanted in the wounds except an open control wound. All wounds were covered with medical Tegaderm to protect from contamination. The closure of wounds were observed and the wound edges were depicted every 2~3 days. See FIG. 4, A. Image J software were used to measure the wound sizes at various time points along with the path of wound healing. See FIG. 4, B.

Figure 4:
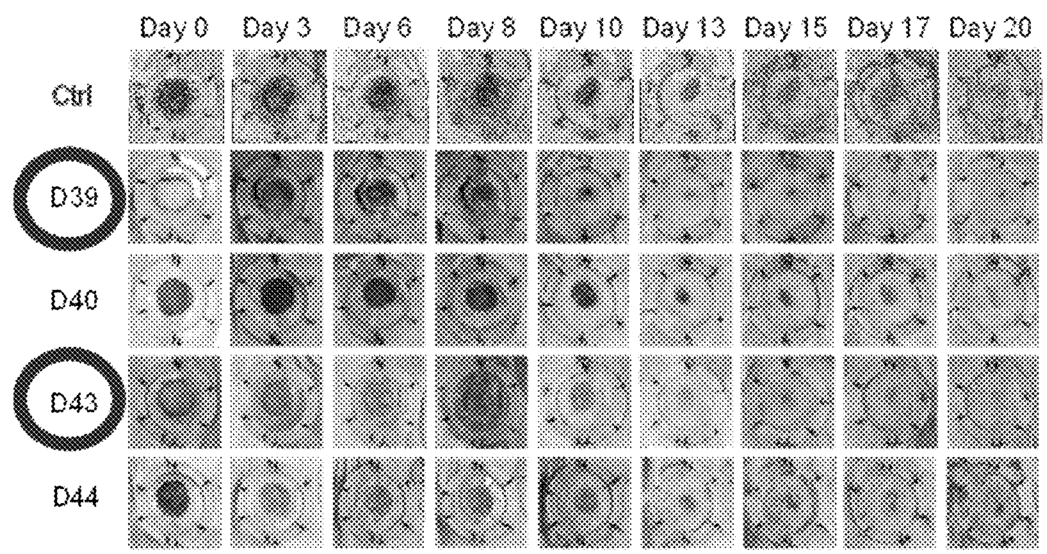
FIG. 4 is a set of figures (A and B) showing the effects of various cell tissue gels on wound healing. Ctrl—open wound; D39—39.5 mg/mL collagen; D40—35 mg/mL hyaluronan; D43—39.5 mg/mL collagen with 3 mg/mL hyaluronan; D44—39.5 mg/mL collagen with 20 mg/mL hyaluronan. 1500 kDa hyaluronan was used in this study. A. Images of the wounds. B. Wound sizes.
Figure 4:
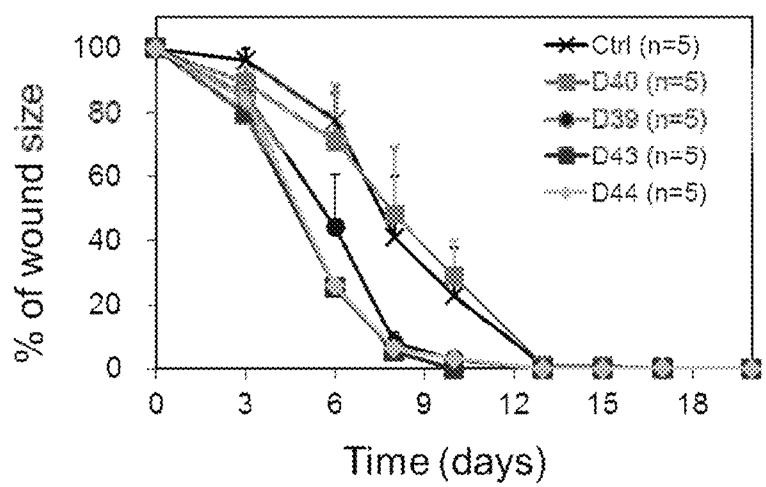

As shown in FIG. 4, B, at day 6, while 78% of wound area remained unhealed in untreated wound, less than 40% of wound area remained unhealed in the wounds treated with collagen-hyaluronan cell tissue gels. The results indicated that the cell tissue gels can accelerate wound healing in mice with full-thickness skin wounds.

Figure 5:
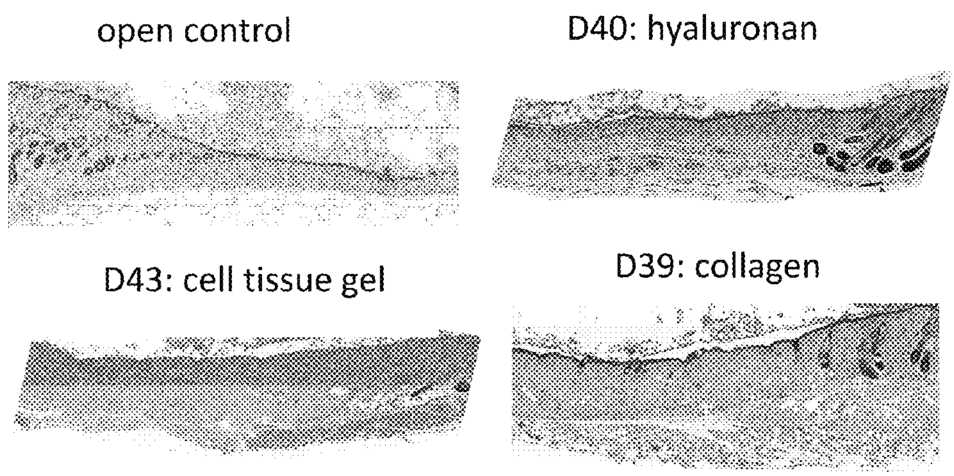
FIG. 5 is a set of images showing the histology of full-thickness wound matrices taken at one month (A) and two months (B) post-operation. The wounds were implanted with various cell tissue gels. control: none, D40: 35 mg/mL hyaluronan, D39: 39.5 mg/mL collagen, D43: 39.5 mg/mL collagen with 3 mg/mL hyaluronan.
Figure 5:
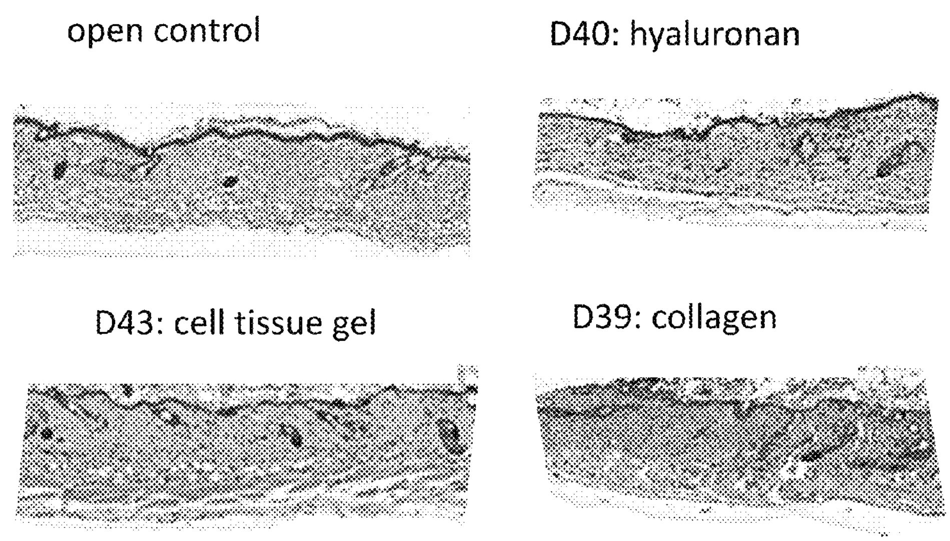

The neo-tissues at wound area were taken for histology analysis at the end of first and second months post-operation. See FIG. 5. The results demonstrated that the wounds filled with cell tissue gels have restored the full-thickness stromal layer before the end of the first month and the regenerated tissue at the end of the second month was very similar to the peripheral normal skin. The result of the cell tissue gels on stromal layer restoration was very distinct from the wounds just filled with hyaluronan or collagen alone.

Example 8: Effects of Cell Tissue Gels on Wound Healing in Diabetic Subjects

Diabetic mice were established in strain FVB with intraperitoneal injections of low doses of Streptozotocin (STZ) for 5 consecutive days (50 mg/kg body weight) to induce diabetes in laboratory mice. A week later, above 250 mg/dl of blood glucose in mice detected for two consecutive days were defined as diabetic mice.

Figure 6:
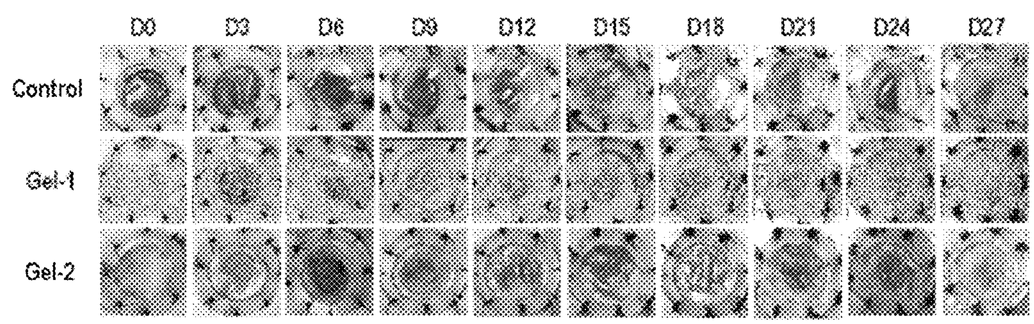
FIG. 6 is a set of figures (A and B) showing the effects of cell tissue gels on wound healing in diabetic subjects. Control: open wound; Gel-1: 50 mg/ml collagen, 5 mg/ml hyaluronan, and 4 mg/ml neomycin; Gel-2: 37.4 mg/mL collagen and 35 mg/mL hyaluronan. A. Images of the wounds. B. Wound sizes.
Figure 6:
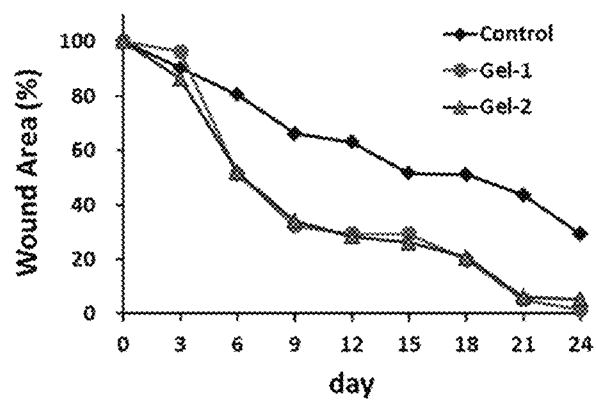

All the animal protocols were pre-approved by the Institutional Animal Care and Use Committee. The full thickness wounds with 6 mm in diameter were created in the dorsal skin of mice. An O-ring with 8 mm in diameter was sutured on the outer of the 6 mm wounds to avoid over contraction of wounds. Different formulations of cell tissue gels were applied to the wounds and medical Tegaderm were used to protect the wounds from contamination. Image J software were used to measure the wound sizes at various time points along with the path of wound healing. See FIG. 6.

A month may be required to heal the 6 mm diabetic wounds in comparison to 13 days for the normal skin wound control. The diabetic wounds were healed at day 18 to day 25 with the implantation of the cell tissue gels containing 20 or 50 mg/mL collagen and 1, 5, 10, 20, 30, or 50 mg/mL hyaluronan. The fastest healing was observed with cell tissue gels further containing vitamins B complex and C. Those wounds healed between day 12 to day 20.

Example 9: Effects of Cell Tissue Gels on Wound Healing in a Pig Model

A porcine wound array model was used to quickly screen the effects of selected cell tissue gels on wound healing. Lanyu pigs at two-month-old or older were used and the study protocol was approved by the Livestock Research Institute Animal Use Committee.

Figure 7:
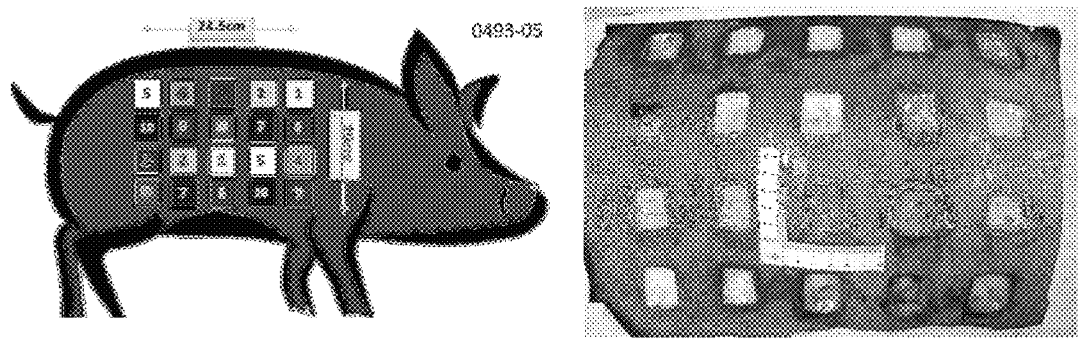
FIG. 7 is a set of pictures showing a porcine wound array model

At least 20 full-thickness excised wounds were made on either the flank or the back. The efficacy of various formulations of cell tissue gels on wound closure was measured. All wounds were covered with medical Tegaderm to protect from contamination. Wound closures were observed and the wound edges were depicted every 2-3 days. Image J software were used to measure the wound sizes at various time points along with the path of wound healing. See FIG. 7.

At the third day after wound creation, fibroblasts were observed to appear in the subcutaneous fat layer, although the cell number was not large and no significant difference among different formulations of cell tissue gels was observed. At the fifth day post-operation, fibroblast proliferation and migration toward the granulation tissue became apparent. Although fibroblasts were still far away from the epithelial side of each wound at the fifth day, the migration distance and cell number of fibroblasts were proportional to the amount of hyaluronan in the cell tissue gel. See Table 3.

TABLE 3

| Group | Infiltration distance of fibroblasts to granulation tissue | Numbers of fibroblasts |
|---|---|---|
| Open wound | + | + |
| 50 mg/mL collagen | ++ | ++ |

TABLE 3-continued

| Group | Infiltration distance of fibroblasts to granulation tissue | Numbers of fibroblasts |
|---|---|---|
| 50 mg/mL collagen, 5 mg/mL hyaluronan | +++ | +++ |
| 50 mg/mL collagen, 10 mg/mL hyaluronan | ++++ | ++++ |
| 50 mg/mL collagen, 15 mg/mL hyaluronan | ++++ | ++++ |
| 50 mg/mL collagen, 20 mg/mL hyaluronan | +++++ | +++++ |
| 50 mg/mL collagen, 30 mg/mL hyaluronan | +++++ | +++++ |

Figure 8:
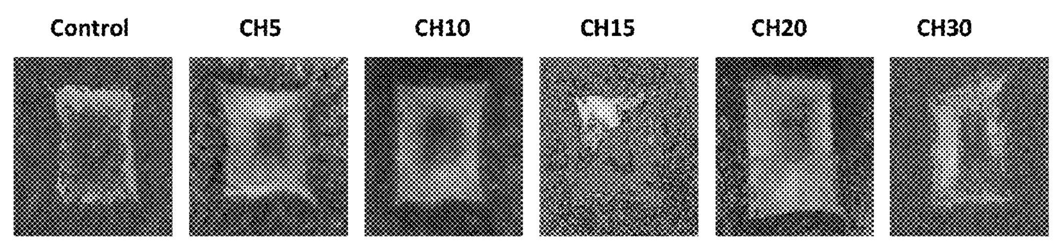
FIG. 8 is a set of pictures showing wounds on a porcine would array model. All wounds were closed by re-epithelialization. The dark area within each lighter rectangle wound area indicates granulation tissues left for further healing process. Control—open wound, CH5, 10, 15, 20, 30-cell tissue gels containing 50 mg/mL collagen and 5, 10, 15, 20, 30 mg/mL hyaluronan, respectively, with 2 mM neomycin.

The appearance of regenerated skin implanted with various cell tissue gels were observed at day 18 post-implantation. See FIG. 8. The cell tissue gels at various formulations promoted the healing process and which were distinct from the open control.

Figure 9:
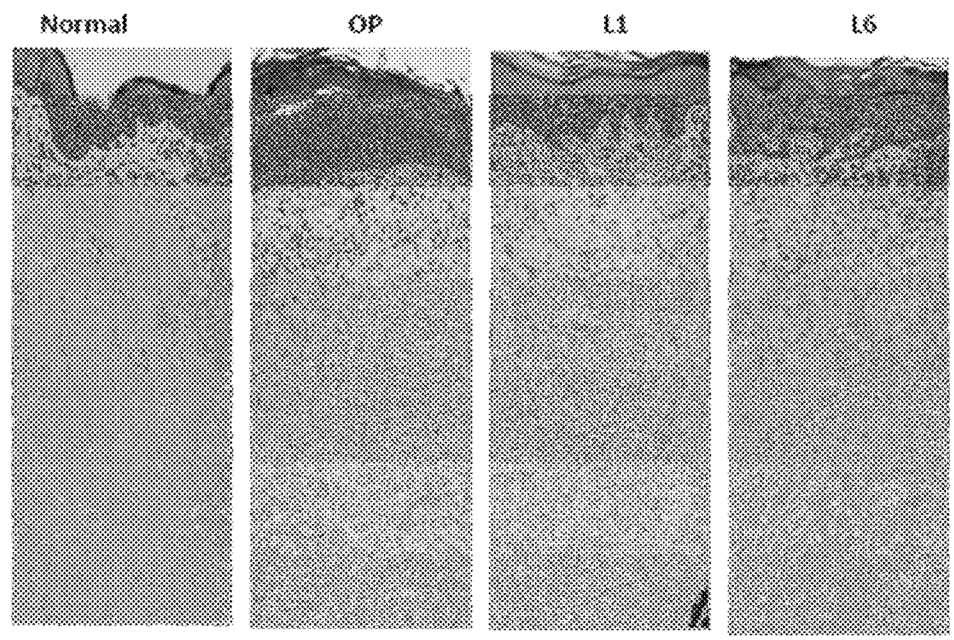
FIG. 9 is a set of images showing the histology of wounds in the pig model. A, two months, B, six months, after the implantation of a cell tissue gel.
Figure 9:
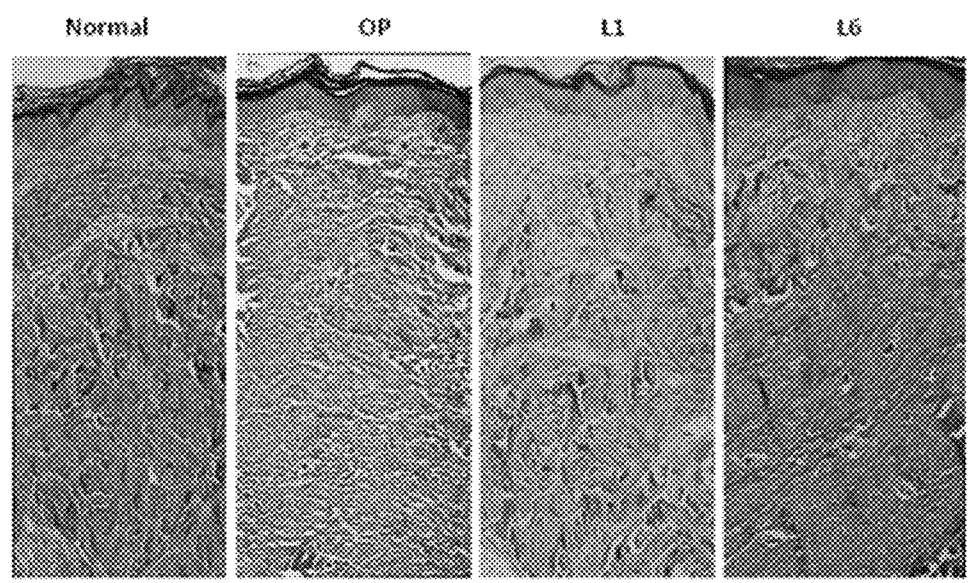

In contrast to the open control, at month 2, the cell tissue gel groups (as L6 with collagen and hyaluronan) demonstrated a good quality of healing in histology that was similar to the normal skin. See FIG. 9, A. At month 6, it was noticed that the thickness and histological characteristics in epithelial layer were most similar to the normal skin. See FIG. 9, B. The architecture of extracellular matrix, including collagen fibrils and elastin, as well as cell numbers and distribution within the stromal layer also showed similarity to the normal skin.

The healing efficacy of various tissue gel formulations was also analyzed by histology in the pig model. The formulations that were tested included: L10: 68 mg/mL collagen and 5 mg/mL hyaluronan with 4 mg/mL neomycin; L11: 35 mg/mL collagen and 3 mg/mL hyaluronan with 4 mg/mL neomycin, and lecithin and glycerin as excipients; L12: 35 mg/mL collagen and 20 mg/mL hyaluronan with 4 mg/mL neomycin, and lecithin and glycerin as excipients; L13: 35 mg/mL collagen and 10 mg/mL hyaluronan with 4 mg/mL neomycin, and lecithin and glycerin as excipients; and L14: 35 mg/mL collagen and 5 mg/mL hyaluronan with 4 mg/mL neomycin, and lecithin and glycerin as excipients.

Transverse sections were cut through the central part of the wounds, including adjacent uninjured skin and underlying muscular tissue, followed by fixation in buffered formalin and embedding in paraffin. Sections were stained with hematoxylin and eosin and examined in a blinded fashion using light microscopy. The healing quality was further examined through Masson's and Verhoff's staining for neomatrix regeneration, organization, and elastin fiber formation.

Figure 10:
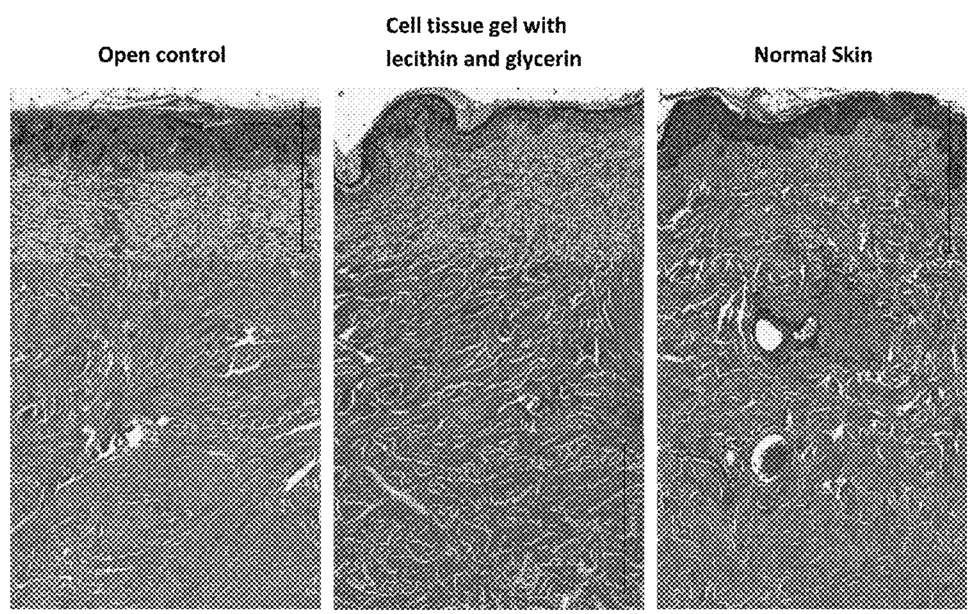
FIG. 10 is an image showing the histology of healing wounds in the pig model.

At 6 months post operation, there were no significant differences on the architecture of neomatrices between normal skin and the L10~L14-treated skin. See FIG. 10. There was a difference between the open control group, which had somewhat thinner collagen fibrils in comparison to the normal skin.

The excipients made the cell tissue gels worked as a cream to smoothen the skin if there were shallow cutaneous wounds. There was no significant difference in the histology of healed matrices among the L10- and L11~14-treated groups.

Example 11: Shallow Skin Wounds

For the healing of shallow skin wounds, cell tissue gels were prepared by mixing excipients with collagen (30 mg/mL), 1500 kDa hyaluronan (5, 10, 20, 30 mg/mL), with or without vitamins, with or without growth factors, and antibiotics such as neomycin (4 mg/mL) or anti-microbial peptide such as pexiganan or its analogs. For example, the contents of the above cell tissue gel were fixed with glycerin and lecithin, and after adjusting the pH to weak-acidic to neutral pH, the mixture was mixed until a homogeneous gel was formed. The gel can adhered to the skin surface after being applied to the skin.

When such a tissue gel is applied to a full-thickness wound, the presence of excipients may not promote the healing speed but keep the wounds in a moist and oily state. Such a formulation is more suitable for partial wounds or first intention wound healing. See Table 4.

TABLE 4

| Sample | Day 0 | Day 7 | Day 9 | Day 11 | Day 13 | Day 15 |
|---|---|---|---|---|---|---|
| Cell tissue gel with lecithin | 100% | 61.1% | 32.4% | 23.4% | 13.5% | 3.1% |
| Cell tissue gel with glycerin | 100% | 69.0% | 34.8% | 23.4% | 16.2% | 2.0% |
| Cell tissue gel with glycerin and lecithin | 100% | 68.6% | 39.9% | 21.2% | 11.0% | 2.2% |

Example 12: Proliferation of Stem Cells

Figure 11:
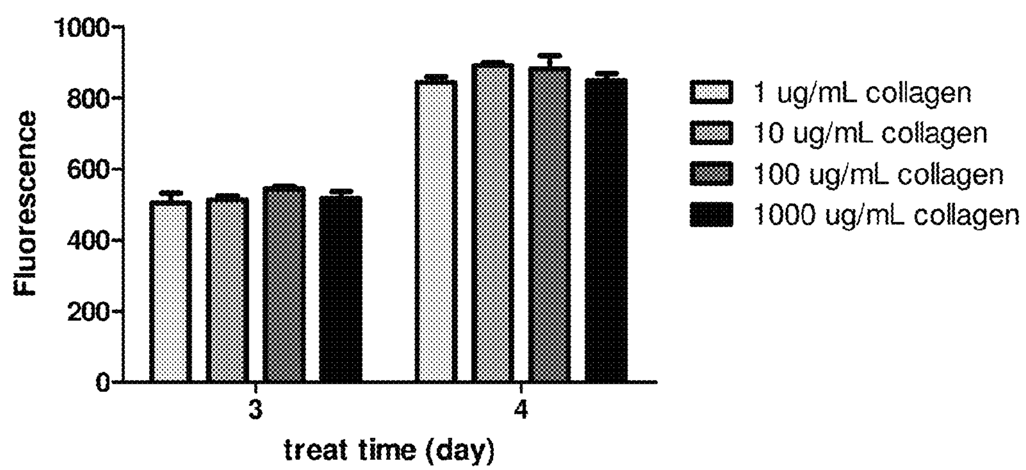
FIG. 11 is a set of bar graphs showing the effect of collagen (A) and hyaluronan (B) on stem cell proliferation.
Figure 11:
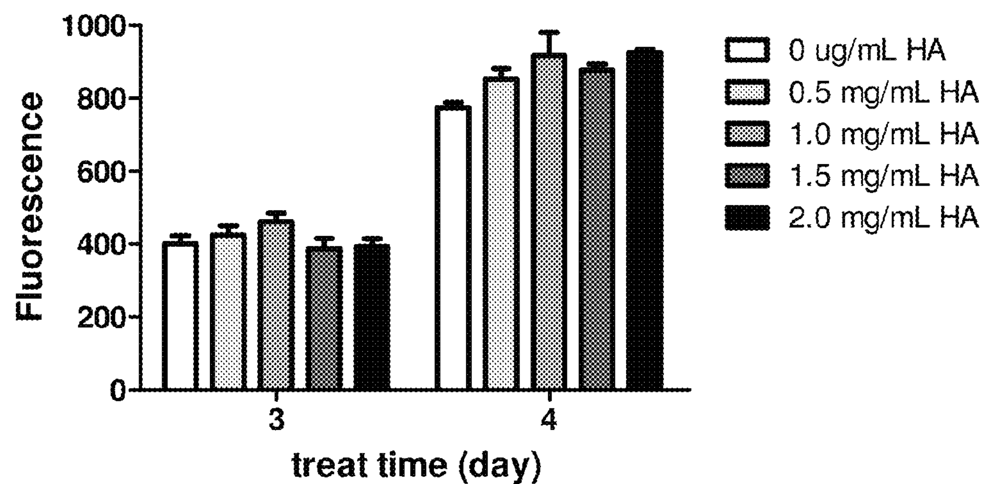

Placenta derived mesenchymal stem cells were culture with cell tissue gels containing collagen and hyaluronan. As shown in FIG. 11, A, collagen had a positive effect on cell proliferation along with time. As shown in FIG. 11, B, increasing concentrations of hyaluronan in cell tissue gels promoted the proliferation of cells; hyaluronan also had a positive effect on cell proliferation along with time. The data suggest that cell tissue gels support cell growth and can be used in the field of regenerative medicine.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A cell tissue gel, consisting of collagen and hyaluronan at a weight ratio of 1:1-15:1, wherein the cell tissue gel promotes wound healing with reduced scarring, and wherein the cell tissue gel is produced by mixing a collagen solution and hyaluronan to obtain a mixture solution containing 20-70 mg/ml of collagen and 3-50 mg/ml of hyaluronan, wherein the mixture is kept at 37° C. of incubator for 30 minutes to allow collagen solidification, whereby the mixture solution forms the cell tissue gel without a cross-linking agent.

2. A cell tissue gel consisting of collagen, hyaluronan, at least one nutrient, and at least one bioactive agent, the weight ratio of the collagen to the hyaluronan being 1:1 to 15:1, wherein the cell tissue gel is produced by mixing a collagen solution, the hyaluronan, the at least one nutrient, and the at least one bioactive agent to obtain a mixture solution containing 20-70 mg/ml of collagen and 3-50 mg/ml of hyaluronan, wherein the mixture is kept at 37° C. of incubator for 30 minutes to allow collagen solidification, whereby the mixture solution forms the cell tissue gel without a cross-linking agent.

3. The cell tissue gel of claim 2, wherein the bioactive agent is a growth factor selected from the group consisting of epidermal growth factor, fibroblast growth factor, vascular endothelial growth factor, connective tissue growth factor, platelet-derived growth factor, insulin-like growth factor, nerve growth factor, hepatocyte growth factor, colony-stimulating factor, stem cell factor, keratinocyte growth factor, granulocyte colony-stimulating factor, granulocyte-macrophage colony-stimulating factor, glial derived neurotrophic factor, ciliary neurotrophic factor, endothelial-monocyte activating polypeptide, epithelial neutrophil activating peptide, erythropoietin, bone morphogenetic protein, brain-derived neurotrophic factor, BRAK, transforming growth factor beta, and tumor necrosis factor.

4. The tissue gel of claim 2, wherein the at least one nutrient is selected from the group consisting of an amino acid, a vitamin, a mineral, a carbon source, a fatty acid, and a cell growth medium.

5. A cell tissue gel, consisting of collagen, hyaluronan, and one or more components selected from the group consisting of at least one nutrient, a bioactive agent, stem cells, and an excipient, and a matrix factor, the weight ratio of the collagen to the hyaluronan being 1:1 to 15:1, wherein the cell tissue gel is produced by mixing a collagen solution, the hyaluronan, and the one or more components to obtain a mixture solution containing 20-70 mg/ml of collagen and 3-50 mg/ml of hyaluronan, wherein the mixture is kept at 37° C. of incubator for 30 minutes to allow collagen solidification, whereby the mixture solution forms the cell tissue gel without a cross-linking agent.

6. The tissue gel of claim 5, wherein the cell tissue gel consists of the collagen, the hyaluronan, and at least one nutrient.

7. The tissue gel of claim 5, wherein the cell tissue gel consists of the collagen, the hyaluronan, at least one nutrient, and stem cells.

8. The tissue gel of claim 5, wherein the cell tissue gel consists of the collagen, the hyaluronan, at least one nutrient, stem cells, and an excipient.

9. A method of treating a skin wound in a subject in need thereof, comprising applying to the skin wound the cell tissue gel of claim 1, wherein the cell tissue gel accelerates wound closure by re-epithelialization and granulation tissue formation relative to applying to the skin wound hyaluronan or collagen alone.

10. The method of claim 9, wherein the subject is a diabetic patient.

* * * * *